United States Patent [19]
Aleman et al.

[11] Patent Number: 5,811,096
[45] Date of Patent: Sep. 22, 1998

[54] STABLE LIQUID COMPOSITION CONTAINING URATE OXIDASE AND LYOPHILIZED COMPOSITION FOR ITS PREPARATION

[75] Inventors: Claude Aleman, Montpellier; Alain Bayol, Tournefeuille; Thierry Breul, Montpellier; Patrice Dupin, Ramonvill Saint Agne, all of France

[73] Assignee: Sanofi, Paris, France

[21] Appl. No.: 644,163

[22] Filed: May 10, 1996

[51] Int. Cl.⁶ .................................................. A61K 38/44
[52] U.S. Cl. .......................................... 424/94.4; 424/94.3
[58] Field of Search ................................ 424/94.4, 94.3

[56] References Cited

U.S. PATENT DOCUMENTS 3,928,137  12/1975  Monte et al. .
3,997,470  12/1976  Monte et al. .

FOREIGN PATENT DOCUMENTS 0069379   1/1983   European Pat. Off. .
0291060   11/1988  European Pat. Off. .
54-17027  6/1979   Japan .
2-43471   9/1990   Japan .

*Primary Examiner*—Jean C. Witz
*Attorney, Agent, or Firm*—Jacobson, Price, Holman & Stern, PLLC

[57] ABSTRACT

The invention relates to a physically stable, pharmaceutically acceptable liquid composition containing urate oxidase, and from 0.1 mg/ml to 10 mg/ml of Poloxamer 188, in buffered aqueous medium. This composition can be obtained by dissolving a lyophilibate in an aqueous solvent.

23 Claims, 2 Drawing Sheets

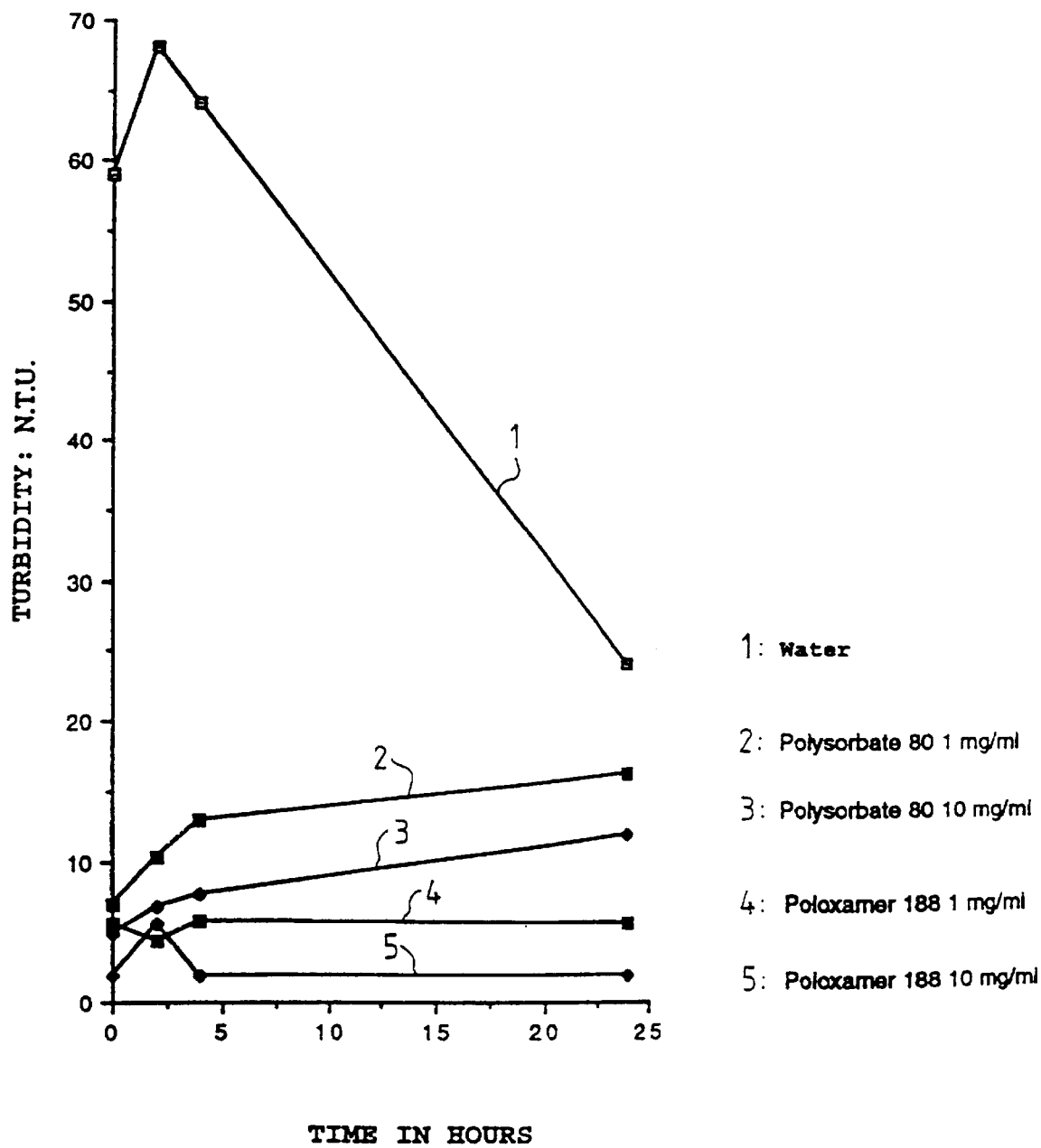

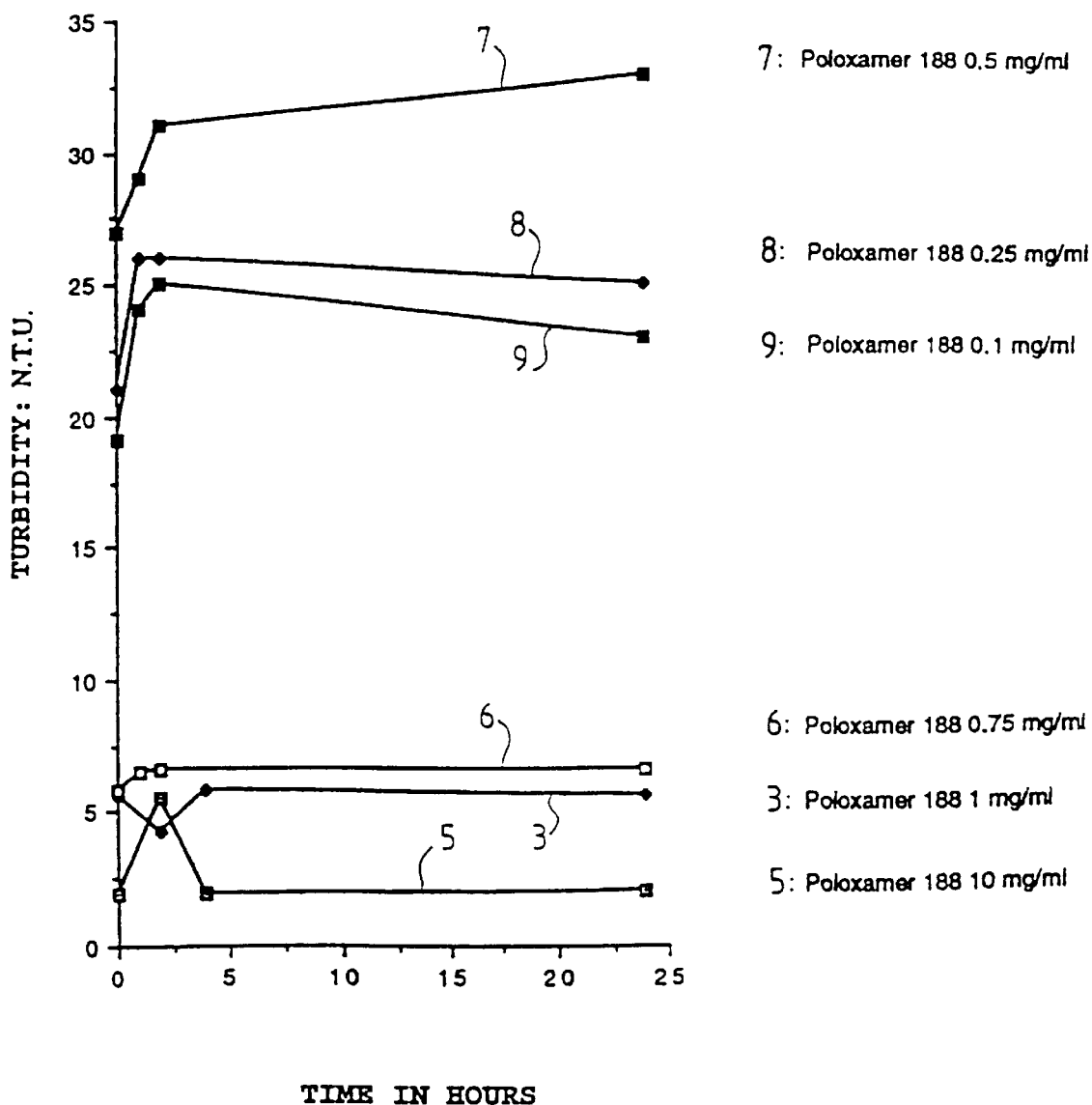

STABLE LIQUID COMPOSITION CONTAINING URATE OXIDASE AND LYOPHILIZED COMPOSITION FOR ITS PREPARATION

The present invention relates to a pharmaceutically acceptable liquid formulation containing urate oxidase which is provided in the form of a solution which is stable at 25° C. and which is clear after stirring.

This solution can also be obtained by dissolving a lyophilisate containing urate oxidase in a solvent.

Urate oxidase (urate oxygen oxidoreductase, EC 1.7.3.3, Uox), a protein enzyme obtained from *Aspergillus flavus* which oxidizes uric acid to allantoin, is used for the prevention or the treatment of hyperuricaemia during chemotherapeutic treatments, because allantoin is ten times more soluble than uric acid and is easily removed by the renal route (Laboureur P. et al., Bull. Soc. Chim. Biol., 1968, 50, 811–825; Kissel P. et al., The Lancet, 1975, J25, 229).

Urate oxidase is a tetramer enzyme composed of four identical units with a molecular weight of 34,152. Each monomer unit, formed from a single polypeptide chain containing 301 amino acids, is acetylated at the N-terminal end and does not have disulphide bridges. The optimum pH for stability of the enzymatic activity of urate oxidase in solution is pH=8 (Bayol A. et al., accepted for publication Biophys. Chem., 1995 (54), 229–35).

The cDNA coding for this protein has been cloned and expressed in *E. coli* (Legoux R. et al., J. Biol. Chem., 1992, 267, (12), 8565–8570), in *A. flavus* (Chevalet L. et al., Curr. Genet., 1992, 21, 447–453) and in *S. cerevisiae* (Leplatois P. et al., Gene., 1992, 122, 139–145). The best yields, obtained from *S. cerevisiae*, favoured the choice of this yeast for the production of recombinant urate oxidase (re-Uox). The recombinant enzyme, accumulated in the intracellular space in a soluble and active form, is extracted and then purified until a pharmaceutical grade is obtained.

In order to obtain a formulation which can be administered to man, the urate oxidase must be prepared in the form of a pharmaceutical composition. Such compositions must retain the enzymatic activity of the urate oxidase over time. Use is generally made of a lyophilized form in order to retain the biochemical integrity and the biological activity of the enzymes under the most varied storage conditions. It is well known that lyophilized preparations retain these properties better than the corresponding liquid preparations.

Lyophilized preparations must be diluted in a pharmaceutically acceptable solvent before administration to man by the parenteral route. A liquid composition containing the enzyme would, nevertheless, be preferable, because it would be able to be administered more rapidly, provided, however, that it is physically and chemically stable.

The known pharmaceutical formulation containing urate oxidase (Uricozyme) is a lyophilized injectable preparation requiring a reconstituting solvent. The composition of the lyophilized form of Uricozyme is as follows:
Urate oxidase . . . 1000 units
8-Aza-2,6-dioxopurine monohydrate
Neutral anhydrous sodium carbonate
Disodium tetracemate dihydrate . . . 0.37 mg
Lactose The composition of the reconstituting solvent is as follows:
Dibasic potassium phosphate
Monobasic potassium phosphate
Glucose
Water for Injections q.s. . . . for 1 ml (Vidal dictionary, Paris, 61st edition, p. 1552, 1985.)

The urate oxidase solution obtained after dissolving the lyophilisate in the reconstituting solvent is seen to increase in turbidity with storage time at 25° C. until a filamentous protein precipitate appears. The formation of this protein precipitate in solution is accelerated by time and the strength of stirring of the solution. The solution obtained is physically unstable.

The solubilizing properties of non-ionic surfaceactive molecules are well known to the person skilled in the art but the interactions between proteins and nonionic surfactants are more specific and are described in the literature.

Patent EP 211 601 describes the use of certain block copolymers, which are non-ionic surface-active molecules, in the stabilization of injectable growth hormone formulations. The growth hormone is stabilized in a gelled matrix formed by a block copolymer containing polyoxyethylene and polyoxypropylene units with a mean molecular weight of between 1100 and 40,000.

U.S. Pat. No. U.S. 4,783,441 describes a method for preventing the denaturation of proteins such as insulin in aqueous solution by addition of an amount which can range up to 500 ppm of surface-active molecules composed of alternating slightly hydrophilic and slightly hydrophobic groups, in solutions with a pH of between 6.8 and 8.

U.S. Pat. No. 5,096,885 describes the composition of a solution to be lyophilized containing human growth hormone, glycine, mannitol, a non-ionic surfactant and a buffer.

The subject of the present invention is a pharmaceutically acceptable liquid composition of a urate oxidase solution containing between 0.1 mg/ml and 10 mg/ml of a block copolymer of ethylene oxide and of propylene oxide, Poloxamer 188, in buffered aqueous medium. This composition is clear and physically and chemically stable after vigorous stirring or after storage for at least 48 hours and up to one year at 25° C.

The advantages offered by this form are greater simplicity of clinical use, which is related to the possibility of being administered directly and of being stored in its directly administrable form for a very long time.

Another advantage lies in the absence of specific instructions for handling precautions which are usually necessary to prevent the precipitation of protein filaments in the solution to be injected, because the composition according to the invention has the property of avoiding the precipitation of protein filaments within the solution.

The aqueous liquid composition of the invention is clear, stable, sterile and pharmaceutically acceptable and can be injected in man or in animals by the subcutaneous, intravenous or intramuscular route.

In the present invention, it is clearly understood that the term urate oxidase denotes the protein obtained by fermentation of a natural strain or of a strain which has been mutated by genetic engineering. The enzyme is therefore produced by extraction of a natural source or from cell cultures. The urate oxidase used in the formulations of the present invention can be obtained, for example, according to the documents U.S. Pat. No. 3,810,820, DD 284 689, DD 296 804, DD 300 781, DE 2 164 018, DE 1 517 742, FR 2 664 286, GB 2 221 910, JP 76-007749, JP-75-030137, JP-84-023987, JP 73 018473, JP-47 029575, SU 565 935, US 4,062,731 or EP 545 688 or according to EP 435 776.

The term pharmaceutically effective amount denotes any amount of urate oxidase which produces a therapeutic effect.

The solutions corresponding to the invention contain a pharmaceutically effective amount of urate oxidase. These solutions preferably contain between 0.1 mg/ml and 50 mg/ml of urate oxidase, depending on the dosage desired. The concentration range of urate oxidase is not critical for the invention and can vary according to the preparations.

The solutions corresponding to the invention contain a non-ionic surfactant of block copolymer of polyoxyethylene and of polyoxypropylene type known as Poloxamer 188 and corresponding to the formula $HO(CH_2CH_2O)_{75}(CH(CH_3)CH_2O)_{30}(CH_2CH_2O)_{75}H$. This product is marketed by the company I.C.I. under the name of Synperonic F 68 and by the company B.A.S.F. under the name of Pluronic F 68. The amounts of Poloxamer 188 necessary for obtaining physically stable urate oxidase solutions are between 0.1 mg/ml and 10 mg/ml and preferably between 0.5 mg/ml and 5 mg/ml.

The pH of the solution is preferably between 7.5 and 8.5. When the pH =8, urate oxidase is particularly stable chemically in solution.

Preference is generally given to the use of a sodium phosphate buffer for buffering the medium. The concentration of the buffer is advantageously from 5 mM to 100 mM.

The buffer preferably used is a sodium phosphate buffer at pH =8 at a concentration of between 5 mM and 100 mM.

The liquid composition according to the invention is preferably isotonic and advantageously comprises excipients necessary for obtaining an isotonic solution, such as mannitol or alanine.

The solution can in particular contain mannitol, preferably at a concentration of between 1 mg/ml and 50 mg/ml.

The solution can in particular contain alanine, preferably at a concentration of between 1 mg/ml and 50 mg/ml.

The solution preferably contains mannitol and alanine in any proportion which retains the isotonicity of the solution, preferably from 1 to 50 mg/ml of mannitol and from 1 to 50 mg/ml of alanine.

The solution advantageously contains approximately 10.6 mg/ml of mannitol and approximately 15.9 mg/ml of alanine.

The liquid composition according to the invention advantageously comprises preservatives necessary for the bacteriological preservation of the solution, such as in particular benzyl alcohol, phenol, meta-cresol, methylparaben, propylparaben, a benzalkonium chloride or benzethonium chloride.

The solution can be obtained directly by dissolving the constituents in water; or after reconstituting a lyophilisate containing the urate oxidase by an aqueous solvent containing the Poloxamer 188; or after reconstituting a lyophilisate containing the urate oxidase and the Poloxamer 188 by an aqueous solvent.

In this respect, another subject of the invention is a lyophilized composition to be dissolved in an aqueous solvent, and containing urate oxidase and Poloxamer 188, the ratio by weight of Poloxamer 188 to urate oxidase being from 0.01 to 50.

The lyophilized composition can advantageously additionally comprise a buffer, as indicated above for the solution.

It can also advantageously comprise excipients which provide for the isotonicity of the aqueous solution obtained by dissolving the lyophilisate in an aqueous solvent, such as for example alanine or mannitol, in amounts which vary according to the volume of reconstituting solvent to be used.

The following examples illustrate the invention without, however, limiting it.

EXAMPLE 1

Urate oxidase solution prepared by dissolving the constituents in water

Urate oxidase . . . 1.5 mg
Mannitol . . . 10.6 mg
L-Alanine . . . 15.9 mg
Dibasic sodium phosphate dodecahydrate . . . 14.32 mg
Poloxamer 188 . . . 1 mg
Water for Injections . . . q.s. for 1 ml

EXAMPLE 2

Urate oxidase solution prepared from a urate oxidase lyophilisate reconstituted by an aqueous reconstituting solvent containing Poloxamer 188.

Composition of the lyophilisate:
Urate oxidase . . . 1.5 mg
Mannitol . . . 10.6 mg
L-Alanine . . . 15.9 mg
Dibasic sodium phosphate dodecahydrate . . . 14.32 mg
Composition of the reconstituting solvent:
Poloxamer 188 . . . 1 mg
Water for Injections . . . q.s. for 1 ml

EXAMPLE 3

Urate oxidase solution prepared from a urate oxidase lyophilisate containing Poloxamer 188 reconstituted by water.

Composition of the lyophilisate:
Urate oxidase . . . 1.5 mg
Mannitol . . . 10.6 mg
L-Alanine . . . 15.9 mg
Dibasic sodium phosphate dodecahydrate . . . 14.32 mg
Poloxamer 188 . . . 1 mg
Composition of the reconstituting solvent:
Water for Injections . . . q.s. for 1 ml The advantages of the compositions of the invention will now be demonstrated by comparison of the properties of various compositions based on urate oxidase, which comparison is summarized in Table I and on the appended figures.

PREPARATION OF THE COMPOSITIONS

The urate oxidase solutions corresponding to the invention can be obtained in various ways, for example:

by mixing a concentrated aqueous urate oxidase solution containing a sodium phosphate buffer at pH =8 with an aqueous solution containing Poloxamer 188 and optionally excipients which provide for the isotonicity of the mixed solution and optionally preservatives.

by dissolving a lyophilisate containing urate oxidase, a sodium phosphate buffer at pH =8 and ballasting excipients which provide for the isotonicity, such as alanine and mannitol, in an aqueous solvent containing Poloxamer 188 and optionally preservatives.

by dissolving a lyophilisate containing urate oxidase, a sodium phosphate buffer at pH =8, ballasting excipients, such as alanine and mannitol, and Poloxamer 188 in an aqueous solvent optionally containing preservatives.

The solutions obtained by these three processes can be sterilely filtered.

They retain their physical stability as well as the chemical stability and the enzymatic activity of the urate oxidase for 1 month at 25° C.

Different analytical methods have been used for measuring different parameters, such as the turbidity or the quantitative determination of the enzymatic activity.

1. Measurement of the turbidity

The turbidity of the urate oxidase solutions is determined by a Ratio Hach turbidimeter. The turbidity results are expressed in Nephelometric Turbidity Units (NTU) defined by: Standard Methods for the Examination of Water and Wastewater of the American Public Health Association. The turbidity measurement indicates the degree of aggregation of the urate oxidase in solution.

2. Quantitative determination of the enzymatic activity of the urate oxidase:

The enzymatic activity of the urate oxidase is determined by spectrophotometry in a thermostatically-controlled cell at 30° C. by monitoring the disappearance of uric acid at 292 nm (Legoux R. et al., J. Biol. Chem., 1992, 267 (12) 8565–8570).

Tests on the stability of the aqueous solution reconstituted according to Example 2 were carried out at 25° C. The stability of aqueous solutions reconstituted by dissolving with water and with solvents containing respectively 1 mg of Polysorbate 80 (Tween 80) or 1 mg of Poloxamer 188 according to the invention, with a sufficient amount of water to produce a volume of aqueous solution of 1 ml, is shown in Table I below.

TABLE I

Stability of the reconstituted aqueous solution at 25° C.

| Time Solvent | 0 | | | 24 hours | | | 48 hours | | |
| --- | --- | --- | --- | --- | --- | --- | --- | --- | --- |
| | Appearance | pH | Enzymatic activity EAU/ml | Appearance | pH | Enzymatic activity EAU/ml | Appearance | pH | Enzymatic activity EAU/ml |
| Water | >IV | 8.01 | 26.1 | >IV | 8.01 | 26.5 | >IV | 8.01 | 27.9 |
| 0.1% Tween 80 | II | 8.0 | 26.0 | II to III | 8.0 | 28.1 | III to IV | 8.0 | 29.1 |
| 0.1% Poloxamer 188 | II | 8.0 | 24.7 | II | 8.0 | 28.9 | II | 8.0 | 28.5 |

EAU: Enzymatic activity unit
The appearance (opalescence) of the solutions is determined in accordance with the method of the European Pharmacopoeia (IX) V. 6 by comparison of the sample to be analysed with a control suspension.

DESCRIPTION OF THE FIGURES

FIG. No. 1 shows the change over 24 hours in the turbidity in NTU, after stirring for 1 minute with a vortex, of five urate oxidase solutions corresponding or not corresponding to the invention, as a function of their contents of non-ionic surfactants.

Composition No. 1:15 mg of urate oxidase, 106 mg of mannitol, 159 mg of L-alanine, 143.2 mg of dibasic sodium phosphate dodecahydrate and 10 ml of Water for Injections.

Composition No. 2:15 mg of urate oxidase, 106 mg of mannitol, 159 mg of L-alanine, 143.2 mg of dibasic sodium phosphate dodecahydrate, 10 mg of Polysorbate 80 and 10 ml of Water for Injections.

Composition No. 4 (according to the invention) 15 mg of urate oxidase, 106 mg of mannitol, 159 mg of L-alanine, 143.2 mg of dibasic sodium phosphate dodecahydrate, 10 mg of Poloxamer 188 and 10 ml of Water for Injections.

Composition No. 3:15 mg of urate oxidase, 106 mg of mannitol, 159 mg of L-alanine, 143.2 mg of dibasic sodium phosphate dodecahydrate, 100 mg of Polysorbate 80 and 10 ml of Water for Injections.

Composition No. 5 (according to the invention): 15 mg of urate oxidase, 106 mg of mannitol, 159 mg of L-alanine, 143.2 mg of dibasic sodium phosphate dodecahydrate, 100 mg of Poloxamer 188 and 10 ml of Water for Injections.

FIG. No. 2 shows the change over 24 hours in the turbidity in NTU, after stirring for 1 minute with a vortex, of six urate oxidase solutions containing Poloxamer 188 according to the invention, as a function of their Poloxamer 188 content.

Composition No. 5:15 mg of urate oxidase, 106 mg of mannitol, 159 mg of L-alanine, 143.2 mg of dibasic sodium phosphate dodecahydrate, 100 mg of Poloxamer 188 and 10 ml of Water for Injections.

Composition No. 4:15 mg of urate oxidase, 106 mg of mannitol, 159 mg of L-alanine, 143.2 mg of dibasic sodium phosphate dodecahydrate, 10 mg of Poloxamer 188and 10 ml of Water for Injections.

Composition No. 6:15 mg of urate oxidase, 106 mg of mannitol, 159 mg of L-alanine, 143.2 mg of dibasic sodium phosphate dodecahydrate, 7.5 mg of Poloxamer 188 and 10 ml of Water for Injections.

Composition No. 7:15 mg of urate oxidase, 106 mg of mannitol, 159 mg of L-alanine, 143.2 mg of dibasic sodium phosphate dodecahydrate, 5 mg of Poloxamer 188 and 10 ml of Water for Injections.

Composition No. 8:15 mg of urate oxidase, 106 mg of mannitol, 159 mg of L-alanine, 143.2 mg of dibasic sodium phosphate dodecahydrate, 2.5 mg of Poloxamer 188 and 10 ml of Water for Injections.

Composition No. 9:15 mg of urate oxidase, 106 mg of mannitol, 159 mg of L-alanine, 143.2 mg of dibasic sodium phosphate dodecahydrate, 1 mg of Poloxamer 188 and 10 ml of Water for Injections.

We claim:

1. A physically stable, pharmaceutically acceptable liquid composition comprising urate oxidase, and from 0.1 mg/ml to 10 mg/ml of Poloxamer 188, in buffered aqueous medium.

2. The composition according to claim 1, comprising between 0.5 mg/ml and 5 mg/ml of Poloxamer 188.

3. The composition according to claim 1, additionally comprising alanine.

4. The composition according to claim 3, wherein the amount of alanine is between 1 mg/ml and 50 mg/ml.

5. The composition according to claim 1, additionally comprising mannitol.

6. The composition according to claim 5, wherein the amount of mannitol is between 1 mg/ml and 50 mg/ml.

7. The composition according to claim 1, additionally comprising alanine and mannitol.

8. The composition according to claim 7, comprising from 1 to 50 mg/ml of alanine and from 1 to 50 mg/ml of mannitol.

9. The composition according to claim 8, comprising 15.9 mg/ml of alanine and 10.6 mg/ml of mannitol.

10. The composition according to claim 1, which is isotonic.

11. The composition according to claim 1, comprising a sodium phosphate buffer.

12. The composition according to claim 1, wherein the concentration of the buffer is between 5 mM and 100 mM.

13. The composition according to claim 1, wherein the pH is between 7.5 and 8.5.

14. The composition according to claim 1, additionally comprising one or more preservatives selected from the group consisting of phenol, benzyl alcohol, metacresol, methylparaben, propylparaben, a benzalkonium chloride and benzethonium chloride.

15. The composition according to claim 1, obtained by dissolving a lyophilisate comprising urate oxidase in an aqueous solvent.

16. The composition according to claim 1, which is sterile and injectable in man or in animals by the subcutaneous, intravenous or intramuscular route.

17. The composition according to claim 15, in a sterile form injectable in man or animals by subcutaneous, intravenous or intramuscular injection, wherein the lyophilisate consists of 1.5 mg of urate oxidase, 10.6 mg of mannitol, 15.9 mg of L-alanine and 14.32 mg of dibasic sodium phosphate dodecahydrate, and the aqueous solvent consists of 1 mg of Poloxamer 188 and water for injection at q.s. for 1 ml.

18. A lyophilized composition for dissolving in an aqueous solvent comprising Poloxamer and urate oxidase at a weight ratio of 0.01 to 50.

19. The lyophilized composition according to claim 18, additionally comprising a buffer.

20. The lyophilized composition according to claim 18, additionally comprising excipients which provide for the isotonicity of the aqueous solution obtained by dissolving the lyophilisate in an aqueous solvent.

21. The composition according to claim 1 obtained by dissolving a lyophilisate comprising the urate oxidase in an aqueous solvent comprising the Poloxamer 188.

22. The composition according to claim 1 obtained by dissolving a lyophilisate comprising the urate oxidase and the Poloxamer 188 in an aqueous solvent.

23. A composition comprising urate oxidase and 0.1–10 mg/ml Poloxamer 188.

* * * * *

UNITED STATES PATENT AND TRADEMARK OFFICE
CERTIFICATE OF CORRECTION

PATENT NO. : 5,811,096
DATED : September 22, 1998
INVENTOR(S) : ALEMAN et al.

It is certified that error appears in the above-identified patent and that said Letters Patent is hereby corrected as shown below:

Title Page: section [30] should be added to show the following --Foreign Application Priority Data - May 11, 1995 [FR] France 9505606.--

Signed and Sealed this

Twenty-eighth Day of March, 2000

Attest:

Q. TODD DICKINSON

*Attesting Officer*  *Commissioner of Patents and Trademarks*